United States Patent [19]

Chang et al.

[11] Patent Number: 5,650,487
[45] Date of Patent: Jul. 22, 1997

[54] SERUM IMMUNOREGULATORY POLYPEPTIDES AND USES THEREFOR

[75] Inventors: Yi-Han Chang, Los Angeles, Calif.; Edward Abraham, Denver, Colo.

[73] Assignee: The Regents of the University of California, Oakland, Calif.

[21] Appl. No.: 455,645

[22] Filed: May 31, 1995

Related U.S. Application Data

[63] Continuation-in-part of Ser. No. 204,486, Mar. 2, 1994, which is a continuation-in-part of Ser. No. 700,110, May 8, 1991, abandoned, which is a continuation of Ser. No. 242,739, Sep. 9, 1988, abandoned.

[51] Int. Cl.$^6$ .............................. C07K 7/00; C07K 14/745
[52] U.S. Cl. ..................... 530/324; 530/300; 530/327; 530/350; 424/185.1
[58] Field of Search .................................... 530/350, 380, 530/395, 300, 324–330; 424/185.1

[56] References Cited

PUBLICATIONS

Kwiatkowski, D. J. et al., Nature 323:455–58, "Plasma and cytoplasmic gelsolins are encoded by a single gene and contain a duplicated actin–binding domain". Oct. 02, 1986.
Abraham et al., "Cellular and humoral bases of hemorrhage-–induced depression of lymphocyte function," *Critical Care Medicine*, vol. 14, No. 2, pp. 81–86, 1986.
McLoughlin et al., "Correlation between anergy and a circulating immunosuppressive factor following major surgical trauma," *Ann. Surg.*, vol. 190, No. 3, pp. 297–304, 1979.
Köhler et al., "Continuous cultures of fused cells secreting antibody of predefined specificity," *Nature*, vol. 256, pp. 495–497, 1975.
Abraham et al., "Effects of hemorrhagic serum on interleukin–2 generation and utilization, " *Critical Care Medicine*, vol. 16, No. 4, pp. 307–311, 1988.
Abraham et al., "The role of interleukin 2 in hemorrhage–induced abnormalities of lymphocyte proliferation," *Circulatory Shock*, 18–205–213 (1986).
Abraham et al., "Generation of functionally active suppressor cells by hemorrhage and haemorrhagic serum," *Clin. exp. Immunol.* (1988) 72, 238–242.

*Primary Examiner*—Thomas M. Cunningham
*Attorney, Agent, or Firm*—Oppenheimer Poms Smith

[57] ABSTRACT

Previously unisolated serum immunoregulatory polypeptides (SIPs) having a molecular weight of approximately 14,000 to 31,000 are provided. The SIPs may be obtained from hemorrhagic serum of mammals and have been shown to activate suppressor T-cells and suppress lymphocyte proliferation and interleukin production. There is a significant homology between SIPs of different mammalian species. The amino acid sequence of an SIP having a molecular weight of about 16,000 is provided. In addition, immunosuppressive polypeptides are identified which have the formula:

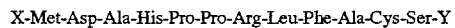

X-Met-Asp-Ala-His-Pro-Pro-Arg-Leu-Phe-Ala-Cys-Ser-Y wherein X is an amino acid sequence having from 0 to 10 amino acids and Y is an amino acid sequence having from 0 to 110 amino acids.

21 Claims, No Drawings

SERUM IMMUNOREGULATORY POLYPEPTIDES AND USES THEREFOR

This is a continuation-in-part of application Ser. No. 08/204,486 filed Mar. 2, 1994; which is a continuation-in-part of Ser. No. 07/700,110 filed May 8, 1991, now abandoned; which is a file wrapper continuation of Ser. No. 07/242/739 filed Sep. 9, 1988, now abandoned.

BACKGROUND OF THE INVENTION

Immunoregulatory agents are substances that regulate or modify the normal or aberrant immune response of a host animal. Such agents are extremely important in medical applications, specifically in diseases that are caused by an abnormal immune response, such as rheumatoid arthritis (RA), systemic lupus erythrematosis (SLE), AIDS, etc. They are also useful where it is desirable to suppress normal immune response, such as in organ transplants and other types of tissue or organ grafts.

Various immunoregulatory agents are known in the art, but all have significant disadvantages. Some examples are cyclophosphamide, methotrexate, 6-MP and cyclosporin A. These drugs suffer from various shortcomings such as toxic side effects and a narrow therapeutic index that severely limits their therapeutic application.

Immune response can be modified in many ways. One of the most desirable approaches is to influence or modulate the activity of suppressor T-cells. Suppressor T-cells are an important class of lymphocyte that have an important role in the regulation of immune response. These cells play an important role in the development of immuno-tolerance. Malfunction of these cells is believed to play a role in the pathogenesis of auto-immune diseases, such as RA and SLE. These diseases are believed to be caused by diminished suppressor T-cell activity and a resultant overproduction of auto-antibodies. This situation may be reversed by activation of suppressor T-cells. In organ transplants, activation of suppressor T-cells, with the consequential suppression of the immune response, helps promote tolerance and prevent rejection of transplanted organs to the recipient's immune system.

Therefore, it would be extremely advantageous to have an immunoregulatory agent that activates suppressor T-cells, thereby regulating immune response, but which has a wide therapeutic index and does not have toxic side effects at physiological doses. The present invention satisfies this need and provides other related advantages.

SUMMARY OF THE INVENTION

The present invention resides in the discovery of previously undescribed and unisolated relatively low molecular weight serum immunoregulatory polypeptides (SIPs) that are present in hemorrhagic mammalian blood. Different mammalian species appear to have different SIPs, and there may be more than one SIP in the blood of each mammalian species. The present invention also relates to synthetic polypeptides which do not naturally occur in hemorrhagic blood, but which exhibit the same serum immunoregulatory properties found in the naturally occurring immunoregulatory peptides which are isolated from hemorrhagic blood in accordance with the present invention. These polypeptides have the formula:

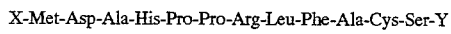

wherein X is an amino acid sequence having from 0 to 10 amino acids and Y is an amino acid sequence having from 0 to 110 amino acids.

The SIPs regulate the immune response in mammals and therefore have far reaching value in the treatment of many diseases, including allograft rejection, auto-immunity, graft versus host diseases, allergies, cancer and AIDS. One mechanism by which the SIPs function to regulate immune response is the activation of suppressor T-cells, resulting in suppression of lymphocyte proliferation. Additionally, the SIPs suppress production of lymphokines, including interleukin-2 (IL-2).

The SIPs of the present invention are low molecular weight compounds, having molecular weights of from approximately 1,500 to approximately 31,000. The SIPs can be obtained from mammalian hemorrhagic serum or produced synthetically. The SIPs isolated from hemorrhagic blood have molecular weights in the range 14,000 to 31,000. The synthetic SIPs, i.e. those not isolated from hemorrhagic blood, have molecular weights of between about 1,500 and 16,000. Hemorrhagic blood is blood obtained from mammals following hemorrhage. Hemorrhagic serum is obtained by allowing hemorrhagic blood to clot, followed by centrifuging and subsequent removal of supernatants. Hemorrhagic serum shows immunoregulatory activity where control samples of normal serum do not.

One SIP was obtained from hemorrhagic serum of rats. The hemorrhagic serum was shown to suppress phytohemagglutinin (PHA) induced proliferation of rat peripheral blood lymphocytes. The active fraction of the hemorrhagic serum was isolated, and activity of the serum showed that the active substance, the SIP, had a molecular weight of approximately 16,000. This SIP has also been isolated from human hemorrhagic blood. The amino acid sequence for this SIP is set forth in SEQ. ID. NO. 1. The SIP set forth in SEQ. ID. NO. 1 has a calculated molecular weight of 16,027 and is a fragment or subunit of gelsolin. Gelsolin is a protein which has been previously isolated from blood. Gelsolin itself does not exhibit immunosuppressive properties.

The SIPs of the present invention have also been shown to suppress the development of cell-mediated and humoral immunity in vivo. SIP treated animals showed significantly lower cell-mediated and humoral immune response to EL cells than control animals.

SIPs also suppress the proliferation of rat peripheral blood mononuclear cells (PBMC). Human SIP was found to suppress PHA-induced proliferation of rat PBMCs. Similarly, rat SIP suppressed PHA-induced proliferation of mouse spleen cells. There is a substantial degree of homology between structure and function of SIP from different species.

The implications of the SIPs of the present invention are far reaching and dramatic because they significantly affect the immune response.

Regarding auto-immune diseases, suppressor T-cells ordinarily block the development of auto-antibodies in auto-immune diseases. There is substantial evidence indicating that auto-immune diseases such as SLE and RA involve a loss of suppressor T-cell activity. Activation of suppressor T-cells using an SIP of the present invention, one mechanism by which the immune response is regulated, is useful in treating such diseases.

It has been firmly established that suppressor T-cells monitory and regulate the immune response. Suppressor T-cells serve teleologically as an "off switch" for the immune response and play an important role in establishing tolerance. For example, it has been shown that suppressor T-cells can replace response with non-response at very low levels of antigen. IL-2, on the other hand, has an opposite effect. Current evidence suggests that exposure to antigen together with appropriate MHC causes unresponsiveness, and that a second signal, IL-2, is required for immunity. Thus, IL-2 converts a "tolerogenic" stimulus into an immunogenic stimulus. By activating suppressor T-cells and decreasing the generation of IL-2, an SIP should promote the establishment of tolerance. This would make the SIPs of the present invention therapeutic in allograft rejection, graft versus host diseases, and in situations in which more subtle effects on the production of lymphokines may be important, such as in allergies or certain types of leukemia that are characterized by requiring IL-2 at certain stages.

Regarding therapeutic applications, it is possible that SIPs may play a role in the pathogenesis of certain immunodeficiency diseases. Monoclonal antibodies against these SIPs may be derived and used to enhance the immune response in such situations.

Preparing monoclonal antibodies directed against the SIPs also has a diagnostic applications. Such antibodies would provide the means for measuring the blood levels of the SIPs, enabling the identification of subgroups of patients who are at particular risk of developing diseases of abnormal immune regulation or developing serious infections after trauma injury.

The following detailed description demonstrates, by way of example, the principles and uses of the present invention.

DETAILED DESCRIPTION OF THE INVENTION

The present invention is embodied in previously undescribed and unisolated serum immunoregulatory polypeptides (SIPs) of molecular weight approximately 1,500 to 31,000 that modulate the immune response in mammals, at least in part by activating suppressor T-cells. The SIPs of the present invention belong to two different groups. The first group has molecular weights of about 14,000 to 31,000 and are isolated from hemorrhagic blood. The second group has molecular weights of about 1,500 to 16,000. The SIPs also suppress lymphocyte proliferation and lymphokine production, including IL-2, in mammals. The first group of SIPs in accordance with the present invention can be obtained from the hemorrhagic blood of various mammals, although rats and a brain-dead human were used for experimentation purposes. Alternatively, the group of lower molecular weight SIPs (1,500 to 16,000) may be prepared synthetically as will be described in detail below.

The SIPs of the present invention have dramatic potential for the effective treatment of a variety of conditions and diseases. For example, suppressor T-cells ordinarily block the development of auto-antibodies in auto-immune diseases, such as SLE and RA. The SIPs, by enhancing activation of these suppressor T-cells, could be useful in treating these diseases.

Suppressor T-cells comprise a class of lymphocytes thought to be distinct from helper and cytolytic T-lymphocytes, whose function is to inhibit the activation phase of immune response (*Cellular and Molecular Immunology*, Abbas, A. K., Lichtman, A. H. and Pober, J. S., 1991). In particular, it is thought that suppressor T-cells inhibit the activation of functionally competent antigen-specific T and/or B lymphocytes.

Suppressor T-cells, which bear CD8 molecules on their surface, may be important in two situations. First, they may be critical for preventing immune responses to self antigens that are not accessible to immature lymphocytes and therefore cannot induce tolerance. For instance, self proteins that do not reach the thymus cannot induce deletion of potentially self-reactive T-cell clones. Second, suppressor cells can inhibit immune response to foreign antigens.

Treatment can be accomplished by various methods. In vitro, the SIP need simply come into physical contact with the suppressor T-cells. In vivo, administration of the SIP may be by various mechanisms that function to bring the SIP into physical contact with the suppressor T-cells, including but not limited to subcutaneous injection, intravenous injection, intraperitoneal injection and delivery via an appropriate pharmaceutical vehicle. The same is true for any cells that are to be treated with an SIP.

Also, IL-2 has been known to convert a tolerogenic stimulus into an immunogenic stimulus. By activating suppressor T-cells and decreasing the generation of IL-2, the SIPs promote tolerance, and would therefore have therapeutic use in allograft rejection cases, graft versus host diseases and other situations characterized by the requirement of IL-2 at various stages. As with suppressor T-cells, treatment can be effected in vitro or in vivo by suitable mechanism to bring the SIP into physical contact with the lymphocytes.

By preparing monoclonal antibodies directed against the SIPs, which can be done using conventional techniques known in the art, the level of these SIPs in blood can be accurately measured using conventional methods.

The SIPs are particularly advantageous because unlike other immunosuppressants, such as cyclosporin A, the SIPs are normal immunoregulatory proteins, and would be expected to have few significant side effects.

The SIPs may be used to treat cells both in vitro and in vivo. In both cases, an effective amount of SIP must be used. For in vitro treatment, 1 µg of SIP per ml of cell medium is effective, but a lower concentration may also be used, depending on the concentration of cells in the medium. The experimentation can be used to determine the lowest effective limit for various cell concentrations. The upper limit for effective treatment is an amount that will not overwhelm the cell medium with too much activity, also determinable by experimentation.

For in vivo treatment, 0.75 mg of SIP per 1 Kg of body weight of mammal I.P. has been found to be effective in mice, but the lowest effective limit may vary from mammal to mammal. This can be easily determined by experimentation, that will not cause so much biological activity in the animal so as to be harmful.

The first group of SIPs in accordance with the present invention were obtained from the hemorrhagic serum of rats and a human, but the serum of other mammals, including but not limited to rabbits, cats, dogs, horses, sheep, monkeys, etc. may be used. Hemorrhagic blood is blood obtained from mammals following hemorrhage. Hemorrhagic serum is obtained by allowing hemorrhagic blood to clot, followed by centrifuging and subsequent removal of supernatants.

Example 1 demonstrates how hemorrhagic serum, containing one of the SIPs of the present invention, was obtained from rats. In order to obtain hemorrhagic serum, 30% of the rats' total blood volume was bled from each animal over a period of 10 minutes. The animals were permitted to recover for two hours, and additional blood samples were taken. These second blood samples constitute hemorrhagic blood, which has been produced by the animal's system after a major hemorrhage (in this case, loss of 30% of total blood volume). Hemorrhagic serum was then obtained by clotting and removal of supernatants. Human hemorrhagic serum was similarly obtained from a brain-dead patient.

It is important to note that hemorrhagic serum can be obtained using other parameters for percent of total blood volume bled and waiting time after blood loss before removing hemorrhagic blood. Although 30% of total blood volume was removed in Example 1, hemorrhagic blood can be obtained by removing as little as 1% or as much as 70% of total blood volume (more than 70% would kill the host animal prior to any opportunity to take a second blood sample). Ten percent (10%) to 40% is preferred. Similarly, although 2 hours elapsed after blood volume loss before removing hemorrhagic blood, as little as a 15-minute time period or as much as 72 hours after initial blood volume removal will also suffice. Thirty (30) minutes to 2 hours is preferred.

The particular method of isolation of the first group of SIPs of the present invention from hemorrhagic blood is not critical. Isolation by chromatography is preferred, including gel electrophoresis or isoelectric focusing (IEF) followed by eluting the SIPs from a gel. Other isolation techniques are known to those skilled in the art and may also be used.

As a feature of the present invention, the portion of the SIP set forth in SEQ. ID. NO. 1 which is responsible for the observed immunosuppressive properties was identified. The amino acid sequence of this immunosuppressive polypeptide is set forth in SEQ. ID. NO. 2. In addition to this particular polypeptide sequence, the present invention covers SIPs having the formula:

X-Met-Asp-Ala-His-Pro-Pro-Arg-Leu-Phe-Ala-Cys-Ser-Y wherein X is an amino acid sequence having from 0 to 10 amino acids and Y is an amino acid sequence having from 0 to 110 amino acids.

A preferred polypeptide is where X is an amino acid sequence having 0 amino acids and Y is an amino acid sequence having 0 amino acids. This polypeptide corresponds to SEQ. ID. NO. 2. The molecular weight of this preferred SIP is about 1,500. Exemplary X amino acid sequences include those where X is Lys; Lys-Lys (SEQ. ID. NO. 3); Asp-Lys-Lys (SEQ. ID. NO. 4); Lys-Asp-Lys-Lys (SEQ. ID. NO. 5); Arg-Lys-Asp-Lys-Lys (SEQ. ID. NO. 6); Pro-Arg-Lys-Asp-Lys-Lys (SEQ. ID. NO. 7); Ser-Pro-Arg-Lys-Asp-Lys-Lys (SEQ. ID. NO. 8); Thr-Ser-Pro-Arg-Lys-Asp-Lys-Lys (SEQ. ID. NO. 9); Arg-Thr-Ser-Pro-Arg-Lys-Asp-Lys-Lys (SEQ. ID. NO. 10); or Tyr-Arg-Thr-Ser-Pro-Arg-Lys-Asp-Lys-Lys (SEQ. ID. NO. 11). Exemplary Y amino acid sequences include those where Y is Asn; Asn-Lys (SEQ. ID. NO. 12); Asn-Lys-Ile (SEQ. ID. NO. 13); Asn-Lys-Ile-Gly (SEQ. ID. NO. 14); Asn-Arg-Ile-Gly (SEQ. ID. NO. 15); Asn-Lys-Ile-Gly-Arg (SEQ. ID. NO. 16); Asn-Lys-Ile-Gly-Arg-Phe (SEQ. ID. NO. 17); Asn-Lys-Ile-Gly-Arg-Phe-Val (SEQ. ID. NO. 18); Asn-Lys-Ile-Gly-Arg-Phe-Val-Ile (SEQ. ID. NO. 19); Asn-Lys-Ile-Gly-Arg-Phe-Val-Ile-Glu (SEQ. ID. NO. 20); Asn-Lys-Ile-Gly-Arg-Phe-Val-Ile-Glu-Glu(SEQ. ID. NO. 21); Asn-Lys-Ile-Gly-Arg-Phe-Val-Ile-Glu-Glu-Val (SEQ. ID. NO. 22); or Asn-Lys-Ile-Gly-Arg-Phe-Val-Ile-Glu-Glu-Val-Pro (SEQ. ID. NO. 23).

The number of amino acids in the X amino acid sequence is preferably 5 or below. However, up to 10 amino acids may be included in the sequence provided that the amino acids are chosen so as not to destroy the immunosuppressive properties of the SIP. Suitable amino acids which may be used in the X amino acid sequence include Lys, Asp, Arg, Pro, Ser and other amino acids with similar structures and chemical properties.

The number of amino acids in the Y amino acid sequence are preferably 10 or below. However, up to 110 amino acids may be present in the Y sequence provided that the amino acids are chosen so as not to destroy the immunosuppressive properties of the SIP. Suitable amino acids which may be used in the Y amino acid sequence include Asn, Arg, Ile, Gly, Lys, Phe, Val, Glu, Pro and other amino acids with similar structures and chemical properties. A preferred SIP is one where the X amino acid sequence has 0 amino acids and the Y sequence has 99 amino acids wherein the amino acids are selected so that the overall polypeptide has a sequence corresponding to SEQ. ID. NO. 1.

The following examples serve to illustrate the present invention.

EXAMPLE 1

Obtaining of Hemorrhagic Serum

The carotid artery of pentobarbital anesthetized rats is catheterized with PE 50 tubing. The tubing is tunneled through the back of the neck and secured with a jacket, tether and swivel apparatus. The rats are then placed in individual cages, given food and water ad libitum, and allowed to recuperate for a minimum of three days. The PHA-induced lymphocyte proliferation response of catheterized-recuperated animals is the same as in normal, uncatheterized control animals (1). To produce hemorrhagic serum, a volume of blood approximately equal to 30% of total blood volume, is bled first from each animal over a 10-minute period. Two hours later, the remaining blood is bled from each animal. Serum obtained from the second sample constitutes "hemorrhagic serum."

Human hemorrhagic serum was similarly obtained from a brain-dead patient before the removal of various organs for transplantation.

EXAMPLE 2

Effect of Hemorrhagic Serum on Milogert-Induced Lymphocyte Proliferation

Procedures as set forth in Example 1 were used to obtain hemorrhagic serum, but with different blood volume loss and waiting periods.

When lymphocytes from normal rats (n=28) were incubated with PHA (125 µg/ml) in the presence of pooled serum collected 2 hours after removal of 30% of total blood volume from three to five rats (hemorrhagic serum), there was a 44% decrease in proliferative response as compared to that present when lymphocytes from the same animal were incubated in the presence of pooled normal serum: $10,084 \pm 2108$ cpm vs. $17,973 \pm 2928$ cpm, p .001.

Similarly, lymphocyte proliferative response was reduced when the cells were incubated (1) in the presence of serum collected 2 hours after removal of 5% of total blood volume and (2) in the presence of serum collected 15 minutes after removal of 30% of total blood volume (see Table 1).

TABLE 1

| Group | Hemorrhage | | 3H update | |
| --- | --- | --- | --- | --- |
| | Volume* | Time** | (cpm × $10^2$ ± SEM) | P |
| Normal (Control) | — | — | 87 ± 11 | 0.001 |
| Hemorrhaged | 5 | 120 | 39 ± 1 | |
| Normal (Control) | — | — | 116 ± 4 | |
| Hemorrhaged | 30 | 15 | 81 ± 6 | 0.001 |

*Volume of hemorrhage, % of TBV
**Minutes post hemorrhage when blood sample was taken

EXAMPLE 3

Isolation of SIP From Rat Hemorrhagic Serum

A serum immunoregulatory polypeptide was isolated from rat hemorrhagic serum by ammonium sulfate precipitation and purified sequentially by Sephadex G-75 chromatography, anion exchange HPLC, and reverse phase HPLC using a C18 column.

Electrophoretically homogeneous SIP can be also obtained by the following procedures:
  (a) ammonium sulfate precipitation—DEAE Sephadex chromatography—Sephadex G-75 chromatography—reverse phase HPLC (C18).
  (b) Amicon filtration—Anion exchange HPLC—Sephadex G-75 chromatography—reverse phase HPLC (C18).

Isolation of SIPs can be accomplished using various methods, with chromatography being preferred.

EXAMPLE 4

Control Phytohemagglutinin (PHA) Induced Lymphocyte Proliferation And Effect of SIP on PHA Induced Lymphocyte Proliferation Phytohemagglutinin (PHA) induced proliferation of rat peripheral blood lymphocytes is assessed by modification of the technique of Keller et al. (2). Blood (approximately 7 ml) is collected from rats in heparinized syringes, diluted 1:6 with 0.9 saline, layered onto 70% Percoil (Pharmacia, Piscataway, N.J.) and centrifuged at 400 g for 30 minutes. The lymphocyte layers are harvested, washed 3 times with RPMI 1640 medium, supplemented with penicillin/streptomycin and adjusted to pH 7.3. Viability, as determined by trypan blue exclusion, is consistently greater than 95%. Lymphocyte purity is greater than 92% as determined by a non-specific esterase stain.

The washed lymphocytes are adjusted to $2.5 \times 10^6$ cells/ml in RPMI 1640 medium supplemented with 5% pooled rat serum or 20% fetal calf serum, penicillin/streptomycin, at pH 7.3. Phytohemagghtinin (Difco, Detroit, Mich.) is added to the cell suspension to produce a final concentration of 125 µg/ml which we have previously found to produce maximal lymphocyte proliferation. Two fifth milliliter (200 µl) of the cell suspension ($5 \times 10^5$ cells) is placed into each well of a flat bottom microliter plate (Falcon 3=040(?) microliter plate, Oxnard, Calif.). All cultures are incubated at 37° C. in a humidified atmosphere at 5% $CO_2$. After 2 days of incubation, 0.2 µCi of 5-($I^{125}$)-2-deoxyuridine (Amersham, Arlington Heights, Ill.) in 25 µl of $10^{-6}$M 5-F-2-deoxyuridine (Sigma, St. Louis, Mo.) in RPMI 1640 is added to each culture. After 18 hours the cells are harvested onto glass fiber filter paper and radioactively assayed in a gamma counter. Uptake of $^{125}I$ is calculated by determining the mean of the triplicate cultures.

The effect of SIPs on PHA-induced proliferation of peripheral blood mononuclear cells (PBMC) was studied in accordance with the techniques described above. The addition of rat SIP into rat PBMC cultures suppressed the proliferation of rat PBMC (control, 22362±2434; SIP, 13536±1645). A substantial degree of homology in structure and function exists between SIPs of different species. Human SIP suppressed PHA-induced proliferation of rat PBMCs (Control, 3974±244; human SIP, 423±145). Rat SIP suppressed PHA-induced proliferation of mouse spleen cells (Control, 94633±10390; rat SIP 65720±11808).

These results show a significant suppression, using an SIP, of the proliferation of rat peripheral blood mononucleus cells. Moreover, the results show substantial homology between SIPs of different species, including humans and rats, and rats and mice. This is of significant importance, as it could enable human lymphocyte proliferation to be controlled by an SIP obtained from the hemorrhagic serum of laboratory animals.

EXAMPLE 5

Determination of Molecular Weight of SIP Obtained From Rat Hemorrhagic Serum

The active fractions of SIP, i.e. fractions that suppressed PHA-induced lymphocyte proliferation in Example 4, obtained from amino exchange HPLC, which showed three bands corresponding to molecular weights of 14,000, 16,000 and 19,000, were further purified by reverse phase HPLC using a C18 column. SDS PAGE analysis of the peak activity fraction showed a single band corresponding to a molecular weight of approximately 16,000 with a possible variation of ±2,000. A substantial component of this single bond is an SIP which has an amino acid sequence that corresponds to SEQ. ID. NO. 1.

EXAMPLE 6

Determination of Molecular Weight of Human Hemorrhagic Serum SIP

A human hemorrhage-induced serum immunoregulatory polypeptide with a molecular weight of 29,000 (also with a possible variation of ±2,000) was similarly isolated and purified from hemorrhagic serum obtained from a brain-dead patient in accordance with the procedures set forth in Examples 1–5.

Minute amounts of this SIP were detected recently in normal blood suggesting that it may be normal immunoregulatory protein. Based on their molecular weight and biological activity, the SIPs of the present invention appear different from inhibitors of cell proliferation reported in the literature including contra-IL-2(6), a 30–100 kd inhibitor of mitogen-induced lymphocyte proliferation found in synovial fluid of patients with rheumatoid arthritis (7), a 70-kd factor which inhibits the production and action of IL-2 (8, 9), a 25 kd inhibitor of IL-1 (10), a 97 kd inhibitor of the response to IL-2 of an IL-2 dependent cell line (11), suppressive factors in serum of patients after trauma and thermal injury (12–16), and others (17–27).

EXAMPLE 7

Effect of SIPs on The Development of Immune Response To $EL_4$ Cells a) $^{51}Cr$ Labelling of $EL_4$ Cells Both the humoral and cellular assays of immune response are based upon the lysis of $^{51}Cr$-labeled $EL_4$ cells. Labelling is carried out essentially according to the method of Canty and Wunderlich (3). To $1 \times 10^8$ $EL_4$. cells in 20% fetal calf serum and Hank's minimum essential medium (HMEM) are added to 60 µCi of $^{51}Cr$. The mixture is incubated for 30 minutes in 20% $CO_2$, at 37° C. The labeled cells are washed three times in HMEM with fetal calf serum to remove unbound $^{51}Cr$ radiolabel and are resuspended in the same medium in a concentration of $1 \times 10^5$ cell/ml.

b) Cell-Mediated Immunity to $EL_4$ Cells

Cell-mediated immunity to $EL_4$ cells is measured according to a previously reported procedure (4). Briefly, spleen cells are obtained from $EL_4$ cell injected or saline injected Lewis rats. The cells are washed and resuspended in HMEM (20% fetal calf serum) to a concentration of $3 \times 10^7$ cells/ml. The spleen cell suspension (0.5 ml) is mixed with $5 \times 10^4$ labeled $EL_4$ cells (0.5 ml) in a 35 mm petri dish (Falcon Plastics) and incubated for 3 hours at 37° C. in 10% $CO_2$ on a rocker platform making 8 reciprocations per minute. The amount of $^{51}Cr$ released from the $EL_4$ cells is then determined. All assays are performed in triplicate.

c) Humoral Immunity

Humoral immunity to $EL_4$ cells is measured by a procedure we have reported previously (4). Briefly, serum from Lewis rats is diluted in HMEM containing fetal calf serum (20%). A 0.2 ml portion of $^{51}Cr$ labeled $EL_4$ cell suspension ($1.25 \times 10^6$ cells/ml) is mixed with 0.3 ml of a 1/6 dilution of rabbit complement (absorbed with $5 \times 10^8$ $EL_4$ cells/ml) and then added to 0.5 ml of serial dilutions of rat sera. The dilution giving 50% lysis of $EL_4$ cells is determined from the van Krogh equation (5) to be the titer of the serum.

d) Effect of SIPs

Effects of SIPs on the development of immune response to $EL_4$ cells were studied. Mice were given 25 μg of SIP or saline (control), I.P., immediately before and 3 days after immunization with $1 \times 10^8$ $EL_4$ cells. Spleen lymphocytes and serum samples were harvested 7 days after immunization and were assayed for cell-mediated and humoral immunity according to a procedure we have reported previously (4). Cell-mediated cytotoxicity was assayed at a 300:1 effector:target cell ratio. Complement-dependent antibody mediated lysis of target cells was assayed at a 100× dilution of serum. Results (Table 2) are expressed as mean SEM. The data show that SIP treated animals have significantly lower cell-mediated as well as humoral immune response than the controls.

TABLE 2

| Treatment Immunity | Cell-Mediated Immunity (% lysis) | Humoral (% lysis) |
| --- | --- | --- |
| Saline | 38.4 ± 2.8 | 36.3 ± 0.9 |
| SIP | 3.1 ± 2.6 | 27.6 ± 4.4 |

EXAMPLE 8

A polypeptide having a sequence corresponding to SEQ. ID NO. 2 was prepared by standard pin-synthesis using F-mocsolid-phase synthesis as described by Geysen, J. M., Meloen, R. H., Bartelip, S. J., "Use of peptide synthesis to probe viral antigens or epitopes to a resolution of a single amino acid. Proc. Natl. Acad. Sci. 1984, 81:3998–4002.

The polypeptide was tested in accordance with Examples 4 found to exhibit suppressive activity.

EXAMPLE 9

A polypeptide having the sequence Met-Asp-Ala-His-Pro-Pro-Arg-Leu-Phe-Ala-Cys-Ser-Asn (SEQ ID NO. 24) is prepared using the same standard amino acid synthesis procedure as was used in Example 8. This polypeptide exhibits immunosuppressive activity when subjected to the assays set forth in Examples 4 and 7.

EXAMPLE 10

A polypeptide having the sequence Lys-Met-Asp-Ala-His-Pro-Pro-Arg-Leu-Phe-Ala-Cys-Ser-Asn (SEQ. ID. NO. 25) is prepared using the same standard amino acid synthesis procedure as was used in Example 8. This polypeptide exhibits immunosuppressive activity when subjected to the assays set forth in Examples 4 and 7.

EXAMPLE 11

A polypeptide having the sequence Met-Asp-Ala-His-Pro-Pro-Arg-Leu-Phe-Ala-Cys-Ser-Asn-Lys-Ile-Gly (SEQ. ID. NO. 26) was prepared using the same standard amino acid synthesis procedure as was used in Example 8. This polypeptide exhibited suppressive activity when subjected to the assays set forth in Examples 4.

EXAMPLE 12

A polypeptide having the sequence Arg-Lys-Asp-Lys-Lys-Met-Asp-Ala-His-Pro-Pro-Arg-Leu-Phe-Ala-Cys-Ser-Asn-Lys-Ile-Gly-Arg (SEQ. ID. NO. 27) is prepared using the same standard amino acid synthesis procedure as was used in Example 8. This polypeptide exhibits immunosuppressive activity when subjected to the assays set forth in Examples 4 and 7.

EXAMPLE 13

A polypeptide having the sequence Arg-Lys-Asp-Lys-Lys-Met-Asp-Ala-His-Pro-Pro-Arg-Leu-Phe-Ala-Cys-Ser (SEQ. ID. NO. 28) is prepared using the same standard amino acid synthesis procedure as was used in Example 8. This polypeptide exhibits immunosuppressive activity when subjected to the assays set forth in Examples 4 and 7.

EXAMPLE 14

A polypeptide having the sequence Met-Asp-Ala-His-Pro-Pro-Arg-Leu-Phe-Ala-Cys-Ser-Asn-Lys-Ile-Gly-Arg (SEQ. ID. NO. 29) is prepared using the same standard amino acid synthesis procedure as was used in Example 8. This polypeptide exhibits immunosuppressive activity when subjected to the assays set forth in Examples 4 and 7.

REFERENCES

1. Abraham, E., Chang Y-H, "The effects of hemorrhage on lymphocyte proliferation," Circ. Shock, 15:141–49 (1985).
2. Keller, S. E., Schleifer, S. J., McKegney, M. P. et al., "A simplified method for assessing phA induced stimulation of rat peripheral blood lymphocytes," J. Immunol. Methods, 51:287–91 (1982).
3. Canty, T. G., Wunderlich, J. R., "Quantitative in vitro assay of cytotoxic cellular immunity," J. Nat. Cancer Inst., 45:761 (1970).
4. Chang Y-H, "Adjuvant polyarthritis I: incorporation of quantitative measures of humoral and cellular immune response," J. Pharmocol. Exp. Ther., 201:1–7 (1977).
5. Kabat, E. A., Mayer, M. M., "Experimental immunochemistry," Springfield, Ill., Charles C. Thomas, p. 136 (1961).
6. Spiegel, J. P., Djew, J. Y., Stock, N. L, Masur, H., Gelmann, E. P., Wuinnan, Jr., G. V., "Sera from patients with acquired immunodeficiency syndrome inhibit production of interleukin-2 by normal lymphocytes," J. Clin. Invest., 75:1957–1964 (1985).
7. Zembala, M., Lemmel, E-M, "Inhibitory factor(s) of lymphoproliferation produced by synovial fluid mononuclear cells from rheumatoid arthritis patients: the role of monocytes in suppression," J. Immunol., 125:1087–1092 (1980).
8. Krakauer, T., "A macrophage derived factor that inhibits the production and action on interleukin 2," J. Leukocyte Biol., 3:429–440 (1985).
9. Miossec, P., Kashiwado, T., and Ziff, M., "Inhibitor of interleukin-2 in rheumatoid synovial fluid," Arth. & Rheum., 30:121 (1987).

10. Arend, W. P., Joslin, F. G., Massoni, R. J., "Effects of the immune complexes on production by human monocytes of interleukin 1 or an interleukin 1 inhibitor," *J. Immunol.,* 134:3868–3875 (1985).
11. Fontana, A., Hengartner, H., deTribolet, N., Weber, E., "Glioblastoma cells release interleukin 1 and factors inhibiting interleukin 1-mediated effects," *J. Immunol,* 132:1837–1844 (1984).
12. Ninneman, J. L., "Immunosuppression following thermal injury through B cell activation of suppressor T cells," *J. Trauma,* 20:206–13 (1980).
13. Constantian, M. B., "Association of sepsis with an immunosuppressive polypeptide in the serum of burn patients," *Ann. Surg.,* 188:209–15 (1978).
14. Ninneman, J. L., Fisher, J. C., Wachtel, T. L., "Thermal injury-associated immunosuppression occurrence and in vitro blocking effect of post-recovery serum," *J. Immunol.,* 122:1736–41.
15. Ninneman, J. L., Condie, J. T., Davis, S. E., Crockett, R. A., "Isolation of immunosuppressive serum components following thermal injury," *J. Trauma.,* 22:834–44 (1982).
16. Aune, T. M., Webb, D. R., Pierce, C. W., "Purification and initial characterization of the lymphokine, soluble immune response suppressor," *J. Immunol.,* 131:2848–54 (1983).
17. Thomas, D. W., Roberts, W. K., Talmage, D. W., "Regulation of the immune response: production of a soluble suppressor by immune spleen cells in vitro," *J Immunol.,* 114:1616–21 (1975).
18. Namba, Y., Waksman, B. H., "Regulatory substances produced by lymphocytes. I. Inhibitor of DNA synthesis in the rat," *Inflammation,* 1:5–12 (1975).
19. Lee, S. C., Lucas, Z. J., "Regulator factors produced by lymphocytes. II. Inhibition of cellular DNA synthesis is associate with a factor inhibiting DNA polymerase-alpha activity," *J. Immunol.,* 118:88–95 (1977).
20. Chiba, K., Nishimura, T., Hashimoto, Y., "Stimulated rat T cell derived inhibitory factor for cellular DNA synthesis (STIF)," *J. Immunol.,* 134:1019–27 (1985).
21. Namba, Y., Waksman, B. H., "Regulatory substances produced by lymphocytes II. Lymphotoxin in the rat," *J. Immunol.,* 115:1018–14 (1985).
22. Greene, W. C., Fleisher, T. H., Waldmann, T. A., "Soluble suppressor supernatants elaborated by concanavalin A-activated human mononuclear cells. I. Characterization by a soluble suppressor of T cell proliferation," *J. Immunol.,* 126:1185–90 (1981).
23. Payan, D. G., Hess, C. A., Goetzl, E. J., "Inhibition by somatostatin of the proliferation of T-lymphocytes and Molt-4 lymphoblasts," *Immunology,* 84:433–41 (1984).
24. Payan, D. G., Goetzl, E. J., "Modulation of lymphocytes function by sensory neuropeptides," *J. Immunol.,* 135:783–875 (1985).
25. Ottaway, C. A., Greenberg, G. R., "Interaction of VIP with mouse lymphocytes: specific binding and the modulation of mitogen responses," *J. Immunol.,* 132:417–24 (1984).
26. O'Dorisio, M. S., Wood, C. L., O'Dorisio, T. M., "Vasoactive intestinal peptide and neuropeptide modulation of the immune response," *J. Immunol.,* 135:792s–98s.

It is apparent from the foregoing that the SIPs of the present invention are extremely effective in regulating the immune response in mammals, as well as in diagnostic applications. Such properties have far reaching and wide therapeutic and diagnostic applications. Therefore, the above examples are given for illustrative purposes only, and the present invention is not to be limited in any way, except as by the appended claims.

---

What is claimed is:

1. A polypeptide having the formula:

X-Met-Asp-Ala-His-Pro-Pro-Arg-Leu-Phe-Ala-Cys-Ser-Y wherein X is an amino acid sequence having from 0 to 5 amino acids and Y is an amino acid sequence having from 0 to 10 amino acids and wherein said polypeptide exhibits suppressive effects on lymphocyte proliferation in vitro.

2. A polypeptide according to claim 1 wherein said polypeptide has the amino acid sequence set forth in SEQ ID NO: 2.

3. A polypeptide according to claim 1 wherein X is an amino acid sequence selected from the group consisting of Lys, SEQ ID NO: 3, SEQ ID NO: 4, SEQ ID NO: 5 and SEQ ID NO: 6.

4. A polypeptide according to claim 1 wherein Y is an amino acid sequence selected from the group consisting of Asn, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20 and SEQ ID NO: 21.

5. A polypeptide according to claim 3 wherein Y is an amino acid sequence selected from the group consisting of Asn, SEQ ID NO: 12, SEQ ID NO: 13, SEQ ID NO: 14, SEQ ID NO: 15 and SEQ ID NO: 16, SEQ ID NO: 17, SEQ ID NO: 18, SEQ ID NO: 19, SEQ ID NO: 20 and SEQ ID NO: 21.

6. A polypeptide having the formula:

X-Met-Asp-Ala-His-Pro-Pro-Arg-Leu-Phe-Ala-Cys-Ser-Y wherein X is an amino acid sequence having SEQ ID NO: 7, SEQ ID NO: 8, SEQ ID NO: 9, SEQ ID NO: 10 or SEQ ID NO: 11 and Y is an amino acid sequence having from 0 to 10 amino acids and wherein said polypeptide exhibits suppressive effects on lymphocyte proliferation in vitro.

7. A polypeptide having the formula:

X-Met-Asp-Ala-His-Pro-Pro-Arg-Leu-Phe-Ala-Cys-Ser-Y wherein X is an amino acid sequence having from 0 to 5 amino acids and Y is an amino acid sequence having SEQ ID NO: 22 or SEQ ID NO: 23 and wherein said polypeptide exhibits suppressive effects on lymphocyte proliferation in vitro.

8. A polypeptide according to claim 6 wherein Y is an amino acid sequence selected from the group consisting of Asn, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20 and SEQ ID NO: 21.

9. A polypeptide according to claim 7 wherein X is an amino acid sequence selected from the group consisting of Lys, SEQ ID NO: 3, SEQ ID NO: 4, SEQ ID NO: 5 and SEQ ID NO: 6.

10. A polypeptide according to claim 1 wherein said polypeptide has the amino acid sequence set forth in SEQ ID NO: 24.

11. A polypeptide according to claim 1 wherein said polypeptide has the amino acid sequence set forth in SEQ ID NO: 25.

12. A polypeptide having the amino acid sequence set forth in SEQ ID NO: 1.

13. A polypeptide according to claim 1 wherein said polypeptide has the amino acid sequence set forth in SEQ ID NO: 26.

14. A polypeptide according to claim 1 wherein said polypeptide has the amino acid sequence set forth in SEQ ID NO: 28.

15. A polypeptide according to claim 1 wherein said polypeptide has the amino acid sequence set forth in SEQ ID NO: 29.

16. A method of modulating immune response in a mammal by administering an immune response effective amount of a polypeptide according to claim 1 to said mammal.

17. A method of modulating immune response in a mammal by administering an immune response effective amount of a polypeptide according to claim 6 to said mammal.

18. A method of modulating immune response in a mammal by administering an immune response effective amount of a polypeptide according to claim 12 to said mammal.

19. A method of preparing monoclonal antibodies using a polypeptide according to claim 1 as an antigen.

20. A method of preparing monoclonal antibodies using a polypeptide according to claim 6 as an antigen.

21. A method of preparing monoclonal antibodies using a polypeptide according to claim 12.

* * * * *

UNITED STATES PATENT AND TRADEMARK OFFICE
CERTIFICATE OF CORRECTION

PATENT NO. : 5,650,487
DATED : July 22, 1997
INVENTOR(S) : Chang et al.

It is certified that error appears in the above-indentified patent and that said Letters Patent is hereby corrected as shown below:

In Column 1, before "BACKGROUND OF THE INVENTION" the following Government acknowledgment should be inserted:

-- This invention was made with Government support under Grant No. GM39102 awarded by the National Institutes of Health. The Government has certain rights in this invention. --

Signed and Sealed this

Fourteenth Day of September, 1999

Attest:

Q. TODD DICKINSON

*Attesting Officer*  Acting Commissioner of Patents and Trademarks

SEQUENCE LISTING ( 1 ) GENERAL INFORMATION:

( i i i ) NUMBER OF SEQUENCES: 29

( 2 ) INFORMATION FOR SEQ ID NO: 1:

( i ) SEQUENCE CHARACTERISTICS:
( A ) LENGTH: 113 amino acids
( B ) TYPE: amino acid
( C ) TOPOLOGY: linear ( i i ) MOLECULE TYPE: protein ( i x ) FEATURE:
( A ) NAME/KEY:
( B ) LOCATION: 1-15
( D ) IDENTIFICATION METHOD:

( x i ) SEQUENCE DESCRIPTION: SEQ ID NO:1:

| Met | Asp | Ala | His | Pro | Pro | Arg | Leu | Phe | Ala | Cys | Ser | Asn | Leu | Ile | Gly | Arg |
|---|---|---|---|---|---|---|---|---|---|---|---|---|---|---|---|---|
| | | | | 5 | | | | | 10 | | | | | 15 | | |
| Phe | Val | Ile | Glu | Glu | Val | Pro | Gly | Glu | Leu | Met | Gln | Glu | Asp | Leu | Ala | Thr |
| | | | 20 | | | | | 25 | | | | | 30 | | | |
| Asp | Asp | Val | Met | Leu | Leu | Asp | Thr | Trp | Asp | Gln | Val | Phe | Val | Trp | Val | Gly |
| 35 | | | | | 40 | | | | | 45 | | | | | 50 | |
| Lys | Asp | Ser | Gln | Thr | Glu | Ala | Leu | Thr | Ser | Ala | Lys | Arg | Tyr | Ile | Glu | Thr |

```
                              55                          60                          65
Asp  Pro  Ala  Asn  Arg  Asp  Arg  Arg  Thr  Pro  Ile  Thr  Val  Val  Lys  Gln  Gly
          70                       75                      80                       85

Phe  Glu  Pro  Pro  Ser  Phe  Val  Gly  Trp  Phe  Leu  Gly  Trp  Asp  Asp  Asp  Tyr
                         90                      95                     100

Trp  Ser  Val  Asp  Pro  Leu  Asp  Arg  Ala  Ala  Ala
          105                      110
```

( 2 ) INFORMATION FOR SEQ ID NO: 2:

( i ) SEQUENCE CHARACTERISTICS:
        ( A ) LENGTH: 12 amino acids
        ( B ) TYPE: amino acid
        ( C ) TOPOLOGY: linear ( i i ) MOLECULE TYPE: protein ( i x ) FEATURE:
        ( A ) NAME/KEY:
        ( B ) LOCATION:
        ( C ) IDENTIFICATION METHOD:

( x i ) SEQUENCE DESCRIPTION: SEQ ID NO: 2:

```
Met  Asp  Ala  His  Pro  Pro  Arg  Leu  Phe  Ala  Cys  Ser
                    5                       10
```

( 2 ) INFORMATION FOR SEQ ID NO: 3:

( i ) SEQUENCE CHARACTERISTICS:
        ( A ) LENGTH: 2 amino acids
        ( B ) TYPE: amino acid
        ( C ) TOPOLOGY: linear ( i i ) MOLECULE TYPE: protein ( i x ) FEATURE:
        ( A ) NAME/KEY:
        ( B ) LOCATION:
        ( C ) IDENTIFICATION METHOD:

( x i ) SEQUENCE DESCRIPTION: SEQ ID NO: 3:

Lys  Lys ( 2 ) INFORMATION FOR SEQ ID NO: 4:

( i ) SEQUENCE CHARACTERISTICS:
        ( A ) LENGTH: 3 amino acids
        ( B ) TYPE: amino acid
        ( C ) TOPOLOGY: linear ( i i ) MOLECULE TYPE: protein ( i x ) FEATURE:
        ( A ) NAME/KEY:
        ( B ) LOCATION:
        ( C ) IDENTIFICATION METHOD:

( x i ) SEQUENCE DESCRIPTION: SEQ ID NO: 4:

Asp  Lys  Lys ( 2 ) INFORMATION FOR SEQ ID NO: 5:

( i ) SEQUENCE CHARACTERISTICS:
        ( A ) LENGTH: 4 amino acids
        ( B ) TYPE: amino acid
        ( C ) TOPOLOGY: linear ( i i ) MOLECULE TYPE: protein ( i x ) FEATURE:

( A ) NAME/KEY:
                    ( B ) LOCATION:
                    ( C ) IDENTIFICATION METHOD:

( x i ) SEQUENCE DESCRIPTION: SEQ ID NO: 5:

Lys Asp Lys Lys ( 2 ) INFORMATION FOR SEQ ID NO: 6:

( i ) SEQUENCE CHARACTERISTICS:
                    ( A ) LENGTH: 5 amino acids
                    ( B ) TYPE: amino acid
                    ( C ) TOPOLOGY: linear ( i i ) MOLECULE TYPE: protein ( i x ) FEATURE:
                    ( A ) NAME/KEY:
                    ( B ) LOCATION:
                    ( C ) IDENTIFICATION METHOD:

( x i ) SEQUENCE DESCRIPTION: SEQ ID NO: 6:

Arg Lys Asp Lys Lys
                5

( 2 ) INFORMATION FOR SEQ ID NO: 7:

( i ) SEQUENCE CHARACTERISTICS:
                    ( A ) LENGTH: 6 amino acids
                    ( B ) TYPE: amino acid
                    ( C ) TOPOLOGY: linear ( i i ) MOLECULE TYPE: protein ( i x ) FEATURE:
                    ( A ) NAME/KEY:
                    ( B ) LOCATION:
                    ( C ) IDENTIFICATION METHOD:

( x i ) SEQUENCE DESCRIPTION: SEQ ID NO: 7:

Pro Arg Lys Asp Lys Lys
                    5

( 2 ) INFORMATION FOR SEQ ID NO: 8:

( i ) SEQUENCE CHARACTERISTICS:
                    ( A ) LENGTH: 7 amino acids
                    ( B ) TYPE: amino acid
                    ( C ) TOPOLOGY: linear ( i i ) MOLECULE TYPE: protein ( i x ) FEATURE:
                    ( A ) NAME/KEY:
                    ( B ) LOCATION:
                    ( C ) IDENTIFICATION METHOD:

( x i ) SEQUENCE DESCRIPTION: SEQ ID NO: 8:

Ser Pro Arg Lys Asp Lys Lys
                        5

( 2 ) INFORMATION FOR SEQ ID NO: 9:

( i ) SEQUENCE CHARACTERISTICS:
                    ( A ) LENGTH: 8 amino acids
                    ( B ) TYPE: amino acid
                    ( C ) TOPOLOGY: linear ( i i ) MOLECULE TYPE: protein ( i x ) FEATURE:
                    ( A ) NAME/KEY:

(B) LOCATION:
(C) IDENTIFICATION METHOD:

(xi) SEQUENCE DESCRIPTION: SEQ ID NO: 9:

Thr Ser Pro Arg Lys Asp Lys Lys
                    5

(2) INFORMATION FOR SEQ ID NO: 10:

(i) SEQUENCE CHARACTERISTICS:
    (A) LENGTH: 9 amino acids
    (B) TYPE: amino acid
    (C) TOPOLOGY: linear (ii) MOLECULE TYPE: protein (ix) FEATURE:
    (A) NAME/KEY:
    (B) LOCATION:
    (C) IDENTIFICATION METHOD:

(xi) SEQUENCE DESCRIPTION: SEQ ID NO: 10:

Arg Thr Ser Pro Arg Lys Asp Lys Lys
                        5

(2) INFORMATION FOR SEQ ID NO: 11:

(i) SEQUENCE CHARACTERISTICS:
    (A) LENGTH: 10 amino acids
    (B) TYPE: amino acid
    (C) TOPOLOGY: linear (ii) MOLECULE TYPE: protein (ix) FEATURE:
    (A) NAME/KEY:
    (B) LOCATION:
    (C) IDENTIFICATION METHOD:

(xi) SEQUENCE DESCRIPTION: SEQ ID NO: 11:

Tyr Arg Thr Ser Pro Arg Lys Asp Lys Lys
                    5                   10

(2) INFORMATION FOR SEQ ID NO: 12:

(i) SEQUENCE CHARACTERISTICS:
    (A) LENGTH: 2 amino acids
    (B) TYPE: amino acid
    (C) TOPOLOGY: linear (ii) MOLECULE TYPE: protein (ix) FEATURE:
    (A) NAME/KEY:
    (B) LOCATION:
    (C) IDENTIFICATION METHOD:

(xi) SEQUENCE DESCRIPTION: SEQ ID NO: 12:

Asn Lys (2) INFORMATION FOR SEQ ID NO: 13:

(i) SEQUENCE CHARACTERISTICS:
    (A) LENGTH: 3 amino acids
    (B) TYPE: amino acid
    (C) TOPOLOGY: linear (ii) MOLECULE TYPE: protein (ix) FEATURE:
    (A) NAME/KEY:
    (B) LOCATION:

( C ) IDENTIFICATION METHOD:

( x i ) SEQUENCE DESCRIPTION: SEQ ID NO: 13:

Asn Lys Ile ( 2 ) INFORMATION FOR SEQ ID NO: 14:

( i ) SEQUENCE CHARACTERISTICS:
        ( A ) LENGTH: 4 amino acids
        ( B ) TYPE: amino acid
        ( C ) TOPOLOGY: linear ( i i ) MOLECULE TYPE: protein ( i x ) FEATURE:
        ( A ) NAME/KEY:
        ( B ) LOCATION:
        ( C ) IDENTIFICATION METHOD:

( x i ) SEQUENCE DESCRIPTION: SEQ ID NO: 14:

Asn Lys Ile Gly ( 2 ) INFORMATION FOR SEQ ID NO: 15:

( i ) SEQUENCE CHARACTERISTICS:
        ( A ) LENGTH: 4 amino acids
        ( B ) TYPE: amino acid
        ( C ) TOPOLOGY: linear ( i i ) MOLECULE TYPE: protein ( i x ) FEATURE:
        ( A ) NAME/KEY:
        ( B ) LOCATION:
        ( C ) IDENTIFICATION METHOD:

( x i ) SEQUENCE DESCRIPTION: SEQ ID NO: 15:

Asn Arg Ile Gly ( 2 ) INFORMATION FOR SEQ ID NO: 16:

( i ) SEQUENCE CHARACTERISTICS:
        ( A ) LENGTH: 5 amino acids
        ( B ) TYPE: amino acid
        ( C ) TOPOLOGY: linear ( i i ) MOLECULE TYPE: protein ( i x ) FEATURE:
        ( A ) NAME/KEY:
        ( B ) LOCATION:
        ( C ) IDENTIFICATION METHOD:

( x i ) SEQUENCE DESCRIPTION: SEQ ID NO: 16:

Asn Lys Ile Gly Arg
                 5

( 2 ) INFORMATION FOR SEQ ID NO: 17:

( i ) SEQUENCE CHARACTERISTICS:
        ( A ) LENGTH: 6 amino acids
        ( B ) TYPE: amino acid
        ( C ) TOPOLOGY: linear ( i i ) MOLECULE TYPE: protein ( i x ) FEATURE:
        ( A ) NAME/KEY:
        ( B ) LOCATION:
        ( C ) IDENTIFICATION METHOD:

( x i ) SEQUENCE DESCRIPTION: SEQ ID NO: 17:

Asn Lys Ile Gly Arg Phe
                  5

( 2 ) INFORMATION FOR SEQ ID NO: 18:

( i ) SEQUENCE CHARACTERISTICS:
        ( A ) LENGTH: 7 amino acids
        ( B ) TYPE: amino acid
        ( C ) TOPOLOGY: linear ( i i ) MOLECULE TYPE: protein ( i x ) FEATURE:
        ( A ) NAME/KEY:
        ( B ) LOCATION:
        ( C ) IDENTIFICATION METHOD:

( x i ) SEQUENCE DESCRIPTION: SEQ ID NO: 18:

Asn Lys Ile Gly Arg Phe Val
                  5

( 2 ) INFORMATION FOR SEQ ID NO: 19:

( i ) SEQUENCE CHARACTERISTICS:
        ( A ) LENGTH: 8 amino acids
        ( B ) TYPE: amino acid
        ( C ) TOPOLOGY: linear ( i i ) MOLECULE TYPE: protein ( i x ) FEATURE:
        ( A ) NAME/KEY:
        ( B ) LOCATION:
        ( C ) IDENTIFICATION METHOD:

( x i ) SEQUENCE DESCRIPTION: SEQ ID NO: 19:

Asn Lys Ile Gly Arg Phe Val Ile
                  5

( 2 ) INFORMATION FOR SEQ ID NO: 20:

( i ) SEQUENCE CHARACTERISTICS:
        ( A ) LENGTH: 9 amino acids
        ( B ) TYPE: amino acid
        ( C ) TOPOLOGY: linear ( i i ) MOLECULE TYPE: protein ( i x ) FEATURE:
        ( A ) NAME/KEY:
        ( B ) LOCATION:
        ( C ) IDENTIFICATION METHOD:

( x i ) SEQUENCE DESCRIPTION: SEQ ID NO: 20:

Asn Lys Ile Gly Arg Phe Val Ile Glu
                  5

( 2 ) INFORMATION FOR SEQ ID NO: 21:

( i ) SEQUENCE CHARACTERISTICS:
        ( A ) LENGTH: 10 amino acids
        ( B ) TYPE: amino acid
        ( C ) TOPOLOGY: linear ( i i ) MOLECULE TYPE: protein ( i x ) FEATURE:
        ( A ) NAME/KEY:
        ( B ) LOCATION:
        ( C ) IDENTIFICATION METHOD:

( x i ) SEQUENCE DESCRIPTION: SEQ ID NO: 21:

```
Asn Lys Ile Gly Arg Phe Val Ile Glu Glu
                 5                      10
```

( 2 ) INFORMATION FOR SEQ ID NO: 22:

( i ) SEQUENCE CHARACTERISTICS:
        ( A ) LENGTH: 11 amino acids
        ( B ) TYPE: amino acid
        ( C ) TOPOLOGY: linear ( i i ) MOLECULE TYPE: protein ( i x ) FEATURE:
        ( A ) NAME/KEY:
        ( B ) LOCATION:
        ( C ) IDENTIFICATION METHOD:

( x i ) SEQUENCE DESCRIPTION: SEQ ID NO: 22:

```
Asn Lys Ile Gly Arg Phe Val Ile Glu Glu Val
                 5                      10
```

( 2 ) INFORMATION FOR SEQ ID NO: 23:

( i ) SEQUENCE CHARACTERISTICS:
        ( A ) LENGTH: 12 amino acids
        ( B ) TYPE: amino acid
        ( C ) TOPOLOGY: linear ( i i ) MOLECULE TYPE: protein ( i x ) FEATURE:
        ( A ) NAME/KEY:
        ( B ) LOCATION:
        ( C ) IDENTIFICATION METHOD:

( x i ) SEQUENCE DESCRIPTION: SEQ ID NO: 23:

```
Asn Lys Ile Gly Arg Phe Val Ile Glu Glu Val Pro
                 5                      10
```

( 2 ) INFORMATION FOR SEQ ID NO: 24:

( i ) SEQUENCE CHARACTERISTICS:
        ( A ) LENGTH: 13 amino acids
        ( B ) TYPE: amino acid
        ( C ) TOPOLOGY: linear ( i i ) MOLECULE TYPE: protein ( i x ) FEATURE:
        ( A ) NAME/KEY:
        ( B ) LOCATION:
        ( C ) IDENTIFICATION METHOD:

( x i ) SEQUENCE DESCRIPTION: SEQ ID NO: 24:

```
Met Asp Ala His Pro Pro Arg Leu Phe Ala Cys Ser Asn
                 5                      10
```

( 2 ) INFORMATION FOR SEQ ID NO: 25:

( i ) SEQUENCE CHARACTERISTICS:
        ( A ) LENGTH: 14 amino acids
        ( B ) TYPE: amino acid
        ( C ) TOPOLOGY: linear ( i i ) MOLECULE TYPE: protein ( i x ) FEATURE:
        ( A ) NAME/KEY:
        ( B ) LOCATION:
        ( C ) IDENTIFICATION METHOD:

( x i ) SEQUENCE DESCRIPTION: SEQ ID NO: 25:

Lys Met Asp Ala His Pro Pro Arg Leu Phe Ala Cys Ser Asn
                  5                              10

( 2 ) INFORMATION FOR SEQ ID NO: 26:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: protein ( i x ) FEATURE:
        ( A ) NAME/KEY:
        ( B ) LOCATION:
        ( C ) IDENTIFICATION METHOD:

( x i ) SEQUENCE DESCRIPTION: SEQ ID NO: 26:

Met Asp Ala His Pro Pro Arg Leu Phe Ala Cys Ser Asn Lys Ile Gly
              5                              10                              15

( 2 ) INFORMATION FOR SEQ ID NO: 27:

( i ) SEQUENCE CHARACTERISTICS:
        ( A ) LENGTH: 22 amino acids
        ( B ) TYPE: amino acid
        ( C ) TOPOLOGY: linear ( i i ) MOLECULE TYPE: protein ( i x ) FEATURE:
        ( A ) NAME/KEY:
        ( B ) LOCATION:
        ( C ) IDENTIFICATION METHOD:

( x i ) SEQUENCE DESCRIPTION: SEQ ID NO: 27:

Arg Lys Asp Lys Lys Met Asp Ala His Pro Pro Arg Leu Phe Ala Cys Ser
                  5                              10                              15
Asn Lys Ile Gly Arg
              20

( 2 ) INFORMATION FOR SEQ ID NO: 28:

( i ) SEQUENCE CHARACTERISTICS:
        ( A ) LENGTH: 17 amino acids
        ( B ) TYPE: amino acid
        ( C ) TOPOLOGY: linear ( i i ) MOLECULE TYPE: protein ( i x ) FEATURE:
        ( A ) NAME/KEY:
        ( B ) LOCATION:
        ( C ) IDENTIFICATION METHOD:

( x i ) SEQUENCE DESCRIPTION: SEQ ID NO: 28:

Arg Lys Asp Lys Lys Met Asp Ala His Pro Pro Arg Leu Phe Ala Cys Ser
                  5                              10                              15

( 2 ) INFORMATION FOR SEQ ID NO: 29:

( i ) SEQUENCE CHARACTERISTICS:
        ( A ) LENGTH: 17 amino acids
        ( B ) TYPE: amino acid
        ( C ) TOPOLOGY: linear ( i i ) MOLECULE TYPE: protein ( i x ) FEATURE:
        ( A ) NAME/KEY:
        ( B ) LOCATION:

(C) IDENTIFICATION METHOD:

(xi) SEQUENCE DESCRIPTION: SEQ ID NO: 29:

Met Asp Ala His Pro Pro Arg Leu Phe Ala Cys Ser Asn Lys Ile Gly Arg
            5                    10                 15